(12) United States Patent
Lin

(10) Patent No.: US 11,471,027 B2
(45) Date of Patent: Oct. 18, 2022

(54) ENDOSCOPE HAVING LARGE FIELD OF VIEW RESULTED FROM TWO FIELD OF VIEWS

(71) Applicant: OmniVision Technologies, Inc., Santa Clara, CA (US)

(72) Inventor: Mei-Chun Lin, Taichung (TW)

(73) Assignee: OmniVision Technologies, Inc., Santa Clara, CA (US)

( * ) Notice: Subject to any disclaimer, the term of this patent is extended or adjusted under 35 U.S.C. 154(b) by 1101 days.

(21) Appl. No.: 15/689,223

(22) Filed: Aug. 29, 2017

(65) Prior Publication Data

US 2019/0059706 A1    Feb. 28, 2019

(51) Int. Cl.
*A61B 1/00*        (2006.01)
*A61B 1/045*       (2006.01)
(Continued)

(52) U.S. Cl.
CPC ...... *A61B 1/00181* (2013.01); *A61B 1/00096* (2013.01); *A61B 1/00177* (2013.01);
(Continued)

(58) Field of Classification Search
CPC ............ A61B 1/00181; A61B 1/00096; A61B 1/00177; A61B 1/00179; A61B 1/00188; A61B 1/045; A61B 1/05; A61B 1/051; A61B 1/0623; A61B 1/00126; A61B 1/0676; A61B 1/0684; A61B 1/0638; A61B 1/00186; A61B 1/0646; G02B 23/243; G02B 27/1066; G02B 27/141; G02B 27/144; G02B 13/06; G02B 23/2423; G02B 27/10; G02B 27/1006; G02B 27/1013; G02B 27/126; G02B 27/142; G02B 2027/0123; G02B 23/2415; G02B 23/2443; G02B 23/2453; G02B 23/2461; G02B 27/28; G02B 6/28; G02B 27/0905; G02B 27/1086; H04N 5/2254
See application file for complete search history.

(56) References Cited

U.S. PATENT DOCUMENTS

| | | | | |
|---|---|---|---|---|
| 3,959,784 | A | * | 5/1976 | Meier ...................... G06K 7/10 |
| | | | | 365/115 |
| 4,467,348 | A | * | 8/1984 | Fujii ......................... H04N 1/46 |
| | | | | 358/78 |
| 2002/0103420 | A1 | * | 8/2002 | Coleman ............ A61B 1/00087 |
| | | | | 600/173 |
| 2008/0304143 | A1 | * | 12/2008 | Jacobsen ............ G02B 23/2423 |
| | | | | 359/371 |

(Continued)

*Primary Examiner* — Michael J Carey
*Assistant Examiner* — Minqiao Huang

(57) ABSTRACT

An endoscope comprises a light splitting device for transmitting a first illuminating light and reflecting a second illuminating light emitted by a light source. The first illuminating light passes through a first color filter transmitting a first color. The second illuminating light passes through the second color filter transmitting a second color. The first color is different from the second color. The light splitting device combines a first incident light of the first color and a second incident light of the second color. The first incident light of the first color and the second incident light of the second color pass through an imaging lens and form images of the first color and the second color on an image sensor, respectively. A CFA (color filter array) comprising a plurality of first CFA components of the first color and a plurality of second CFA component of the second color covering the image sensor.

5 Claims, 8 Drawing Sheets

(51) Int. Cl.
  *A61B 1/05*    (2006.01)
  *A61B 1/06*    (2006.01)
  *G02B 23/24*   (2006.01)
  *G02B 27/14*   (2006.01)
  *G02B 27/10*   (2006.01)
  *G02B 13/06*   (2006.01)

(52) U.S. Cl.
  CPC ...... *A61B 1/00179* (2013.01); *A61B 1/00186* (2013.01); *A61B 1/00188* (2013.01); *A61B 1/045* (2013.01); *A61B 1/05* (2013.01); *A61B 1/051* (2013.01); *A61B 1/0623* (2013.01); *A61B 1/0676* (2013.01); *A61B 1/0684* (2013.01); *G02B 23/243* (2013.01); *G02B 27/1066* (2013.01); *G02B 27/141* (2013.01); *G02B 27/144* (2013.01); *A61B 1/00126* (2013.01); *G02B 13/06* (2013.01)

(56) References Cited

U.S. PATENT DOCUMENTS

| | | | |
|---|---|---|---|
| 2010/0053312 A1* | 3/2010 | Watanabe | A61B 1/043 348/65 |
| 2014/0024951 A1* | 1/2014 | Herzlinger | A61B 5/0084 600/478 |
| 2014/0221749 A1* | 8/2014 | Grant | A61B 1/00183 600/112 |
| 2014/0288369 A1 | 9/2014 | Henley et al. | |
| 2015/0112141 A1 | 4/2015 | Oginski et al. | |
| 2016/0178886 A1 | 6/2016 | Shechterman | |
| 2016/0242631 A1* | 8/2016 | Sholev | A61B 90/98 |
| 2016/0256038 A1 | 9/2016 | Goldfarb et al. | |
| 2016/0345804 A1 | 12/2016 | Wieters et al. | |
| 2017/0055815 A1* | 3/2017 | Woods | H04N 5/2256 |
| 2017/0172663 A1* | 6/2017 | Popovic | G06T 7/30 |

* cited by examiner

US 11,471,027 B2

ENDOSCOPE HAVING LARGE FIELD OF VIEW RESULTED FROM TWO FIELD OF VIEWS

FIELD OF THE INVENTION

This invention relates to an endoscope, and more specifically relates to an endoscope having a large field of view.

BACKGROUND OF THE INVENTION

An endoscope is a medical diagnostic instrument used for imaging a ventricle within a patient. It includes a flexible shaft capable of being inserted into the patient through an orifice thereof. The shaft has a tip that includes a light source and a camera for respectively illuminating and capturing images of part of the patient, such as a body cavity or an organ. The endoscope has a FOV (field of view) by virtue of the camera. An endoscope with a viewing port through the end of the tip is a front view endoscope. An endoscope with a viewing port through a side of the tip is a side view endoscope.

A smaller endoscope would allow a smaller incision and reduce patient's suffering. An endoscope having higher image resolution would provide clearer images which enable more detailed diagnosis. An endoscope having larger FOV would provide more information. Either the front view endoscope or the side view endoscope has a limited FOV. This will limit the effectiveness of an endoscope in diagnosis of the imaged ventricle. Accordingly, endoscopes having large FOV, while the size and resolution do not change, are demanded.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Figure 1:
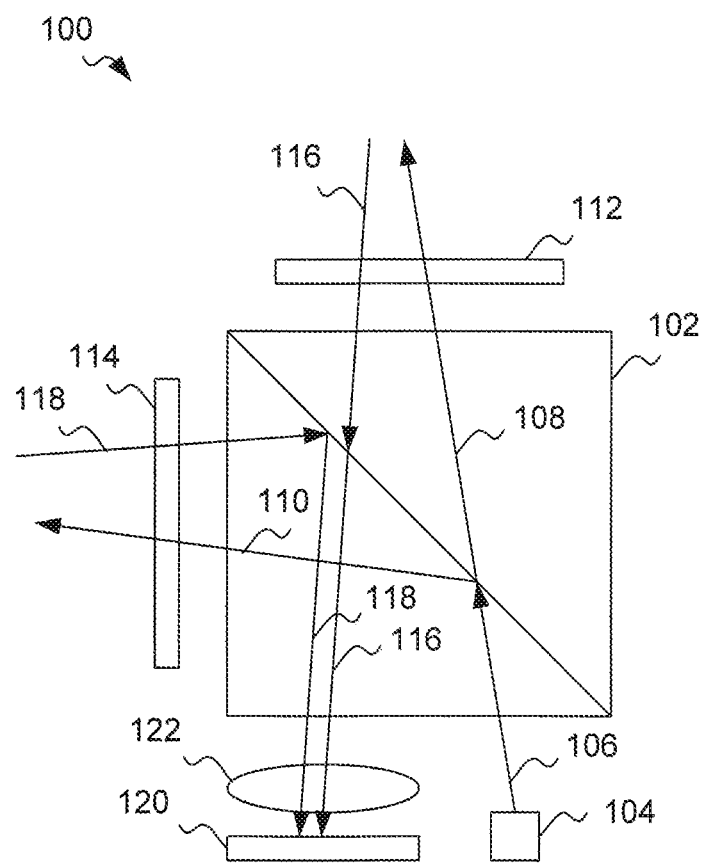
FIG. 1 schematically illustrates an exemplary endoscope according to an embodiment of the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable combinations and/or sub-combinations in one or more embodiments.

FIG. 1 schematically illustrates an exemplary endoscope 100 according to an embodiment of the present invention. A light splitting device 102 transmits a first illuminating light 108, which is a portion of an illuminating light 106 emitted by a light source 104 and reflects a second illuminating light 110, which is also a portion of illuminating light 106 emitted by light source 104. Light splitting device 102 may be a beam splitter cube, a half mirror, a dichroic mirror, or the like. In FIG. 1, for example, light splitting device 102 is represented by a beam splitter cube. Light source 104 may be a white light source. For example, light source 104 may be a white light LED (light emitting diode).

First illuminating light 108 passes through a first color filter 112 transmitting a first color. After passing through first color filter 112, first illuminating light 108 is of the first color. Second illuminating light 110 passes through a second color filter 114 transmitting a second color. After passing through second color filter 114, second illuminating light 110 is of the second color. The first color differs from the second color. For example, first color filter 112 may be a red filter transmitting red color light and absorbing other color light. Second color filter 114 may be a green color filter transmitting green color light and absorbing other color light. It is appreciated that the first color may be red, green, blue, or any color, and the second color may also be red, green, blue, or any color. However, the first color differs from the second color. In an embodiment, light source 104 may comprise a first LED of the first color and a second LED of the second color. In an embodiment, light source 104 may emit illuminating light 106 comprising first illuminating light 108 and second illuminating light 110.

First illuminating light 108 illuminates an object or a part of an object (not shown) and reflected by the object becoming a first incident light 116. Second illuminating light 110 illuminates another object or another part of the object (not shown) and reflected by the other object becoming a second incident light 118. First incident light 116 transmits through first color filter 112 and light splitting device 102, and is incident on an image sensor 120 after passing through an imaging lens 122. Second incident light 118 transmits through second color filter 114, is reflected by light splitting device 102, and is incident on image sensor 120 after passing through imaging lens 122. Light splitting device 102 combines first incident light 116 and second incident light 118. For illustration purpose, first incident light 116 and second incident light 118 are represented by two lines. In reality first incident light 116 and second incident light 118 are overlapping.

Figure 2:
FIG. 2 illustrates an exemplary CFA (color filter array) covering an image sensor according to an embodiment of the present invention.

First incident light 116 of the first color and second incident light 118 of the second color from different directions superimpose at image sensor 120. First incident light 116 passes through imaging lens 122 and forms a first image of the first color on image sensor 120 and second incident light 118 passes through imaging lens 122 and forms a second image of the second color on image sensor 120. To separate first and second images formed by first incident light 116 of the first color and second incident light 118 of the second color, image sensor 120 is covered by a CFA (color filter array) 200 as shown in FIG. 2, according to an embodiment of the present invention. CFA 200 comprises a plurality of first CFA components 202 and a plurality of second CFA components 204.

CFA 200 may comprise a checkerboard pattern of first CFA component 202 and second CFA component 204 as shown in FIG. 2. First CFA component 202 may be a red filter and second CFA component 204 may be a green filter as shown in FIG. 2. First CFA component 202 and second CFA component 204 may be of any colors, however, the color of first CFA 202 must be the same as the color of first color filter 112, and the color of second CFA component 204 must be the same as the color of second color filter 114. It is appreciated that CFA 200 may comprise other patterns, which are not checkerboard patterns, for example, alternate lines and others. Using standard and/or special algorithms, the image under the checkerboard pattern (i.e., CFA 200) detected by image sensor 120, can be interpolated to produce two full separate images of the first and second colors formed by incident light 116 and incident light 118, respectively.

Figure 3:
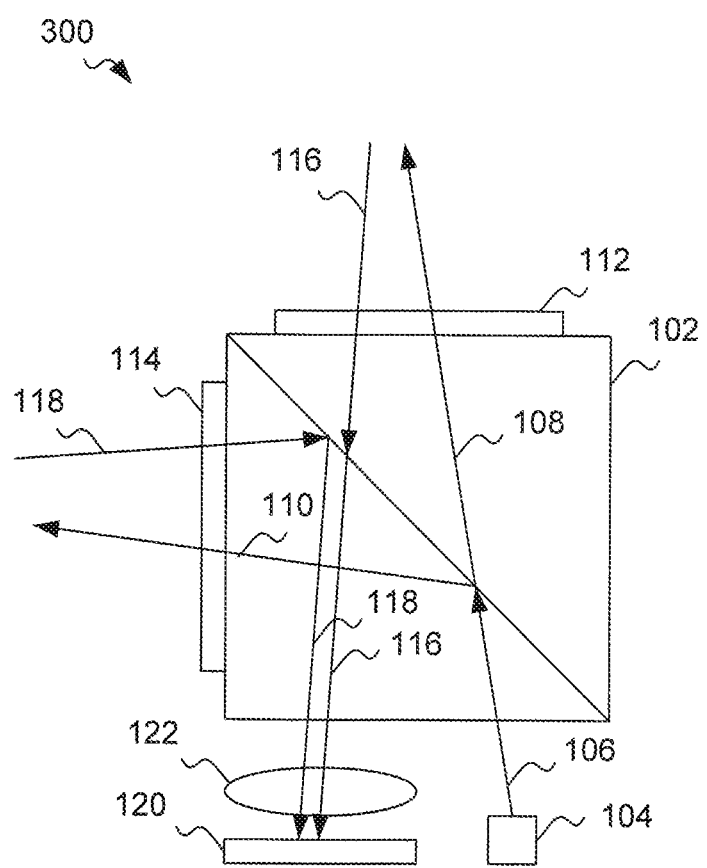
FIG. 3 schematically illustrates an exemplary endoscope using a beam splitter cube according to an embodiment of the present invention.

FIG. 3 schematically illustrates an exemplary endoscope 300 according to an embodiment of the present invention. FIG. 3 is similar to FIG. 1, except the following. Light splitting device 102 is a beam splitter cube (also numbered as 102). First color filter 112 is attached on a first side of beam splitter cube 102, and second color filter 114 is attached on a second side of beam splitter cube 102. The first side and the second side are perpendicular.

Figure 4:
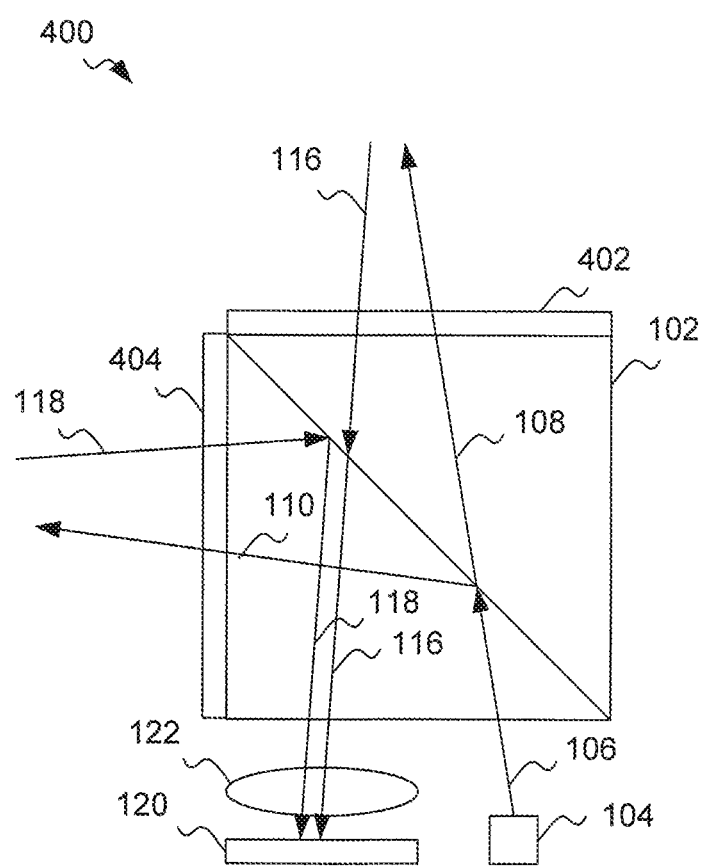
FIG. 4 schematically illustrates an exemplary endoscope using a coated beam splitter cube according to an embodiment of the present invention.

FIG. 4 schematically illustrates an exemplary endoscope 400 according to an embodiment of the present invention. FIG. 4 is similar to FIG. 1, except the following. Light splitting device 102 is a beam splitter cube (also numbered as 102). First color filter 112 is a first band pass multilayer coating 402 that transmits light of the first color and reflects light of other colors. Second color filter 114 is a second band pass multilayer coating 404 that transmits light of the second color and reflects light of other colors.

Figure 5:
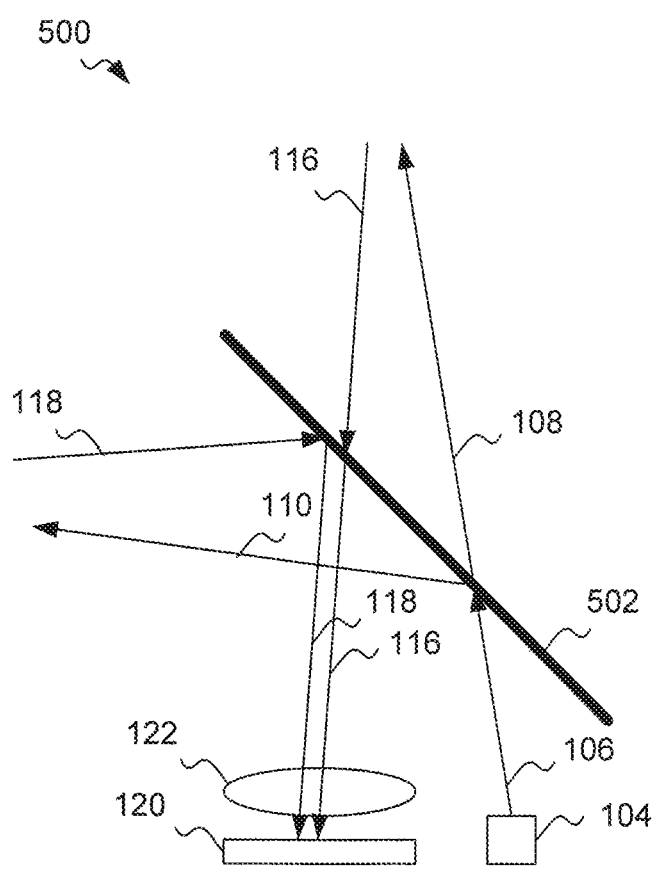
FIG. 5 schematically illustrates an exemplary endoscope using a dichroic mirror according to an embodiment of the present invention.

FIG. 5 schematically illustrates an exemplary endoscope 500 according to an embodiment of the present invention. FIG. 5 is similar to FIG. 1, except the following. Light splitting device 102 of FIG. 1 is a dichroic mirror 502. For example, dichroic mirror 502 transmits light of the first color and reflects light of the second color. Light source 104 may comprise a first LED of the first color and a second LED of the second color.

Figure 6:
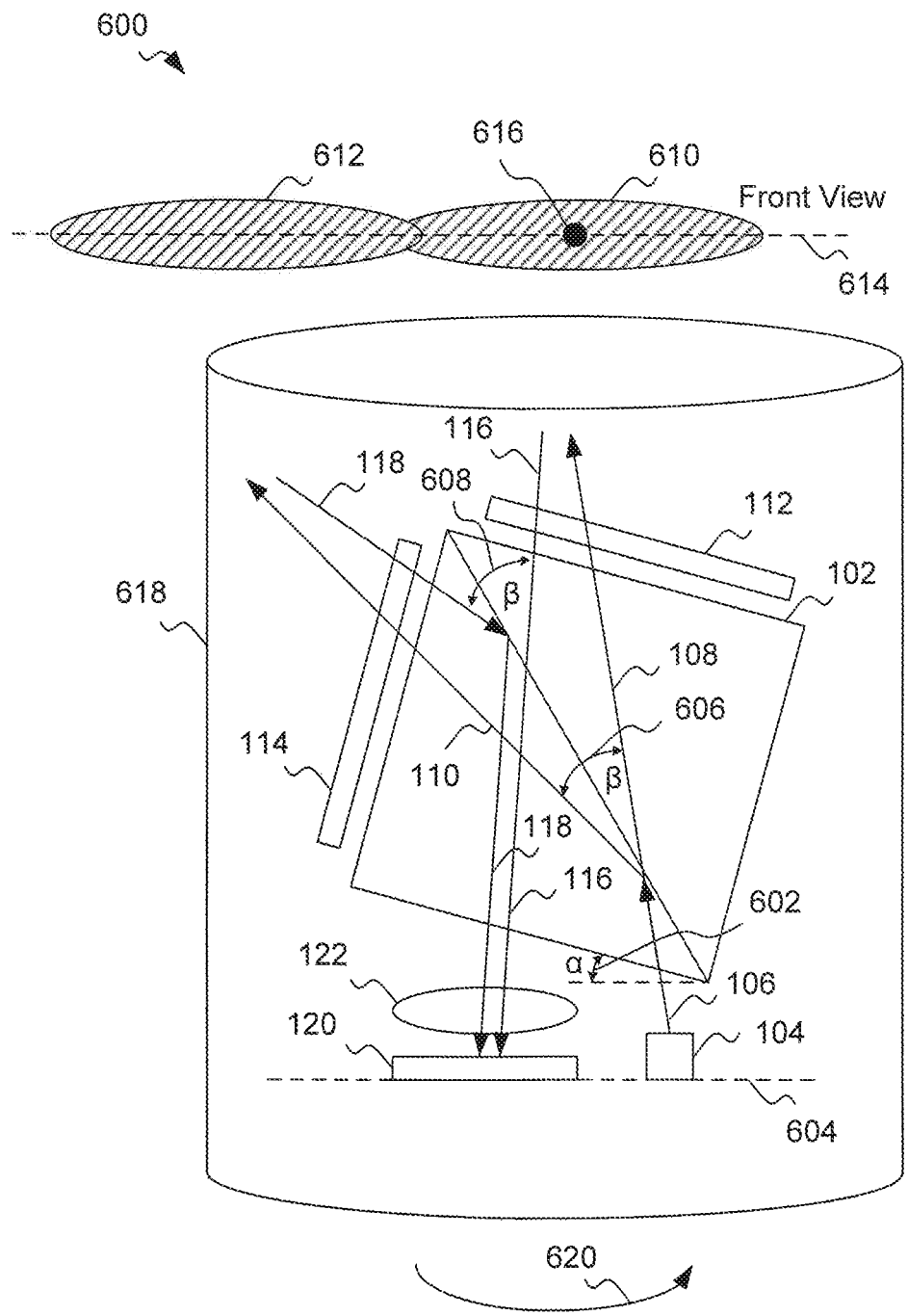
FIG. 6 schematically illustrates an exemplary rotated endoscope using a tilted light splitting device according to an embodiment of the present invention.

FIG. 6 schematically illustrates an exemplary endoscope 600 according to an embodiment of the present invention. FIG. 6 is similar to FIG. 1. However, in endoscope 600, light splitting device 102 is tilted by an angle α 602 relative to a plane 604 of light source 104 and image sensor 120, together with first color filter 112 and second color filter 114. Beam splitter cube 102 of endoscopes 300 and 400, and dichroic mirror 502 of endoscope 500 may be used as well in endoscope 600 replacing light splitting device 102.

First illuminating light 108 represents a chief ray of illuminating light of the first color. Second illuminating light 110 represents a chief ray of illuminating light of the second color. Because light splitting devices 102 is tilted, an angle β 606 between first illuminating light 108 and second illuminating light 110 is less than 90 degree. First incident light 116 and second incident light 118 before combined by light splitting device 102 make a same angle β 608. First incident light 116 is a chief ray of a first image formed by first incident light 116 on image sensor 120. Second incident light 118 is a chief ray of a second image formed by second incident light 118 on image sensor 120. The angle between illuminating light 106 and plane 604 may be adjusted to further control the magnitude of angle β 606 and 608.

In this manner, first incident light 116 provides a first FOV (field of view) 610, and second incident light 118 provides a second FOV 612. In an embodiment, first FOV 610 and second FOV 612 are on a same plane 614 of front view. A distance between first FOV 612 and second FOV 614 is determined by angle β 608.

Light splitting device 102 together with first color filter 112 and second color filter 114, image sensor 120 together with imaging lens 122, and light source 104 are enclosed in a housing 618. Housing 618 may be cylindrical. Housing 618 may be transparent or may comprise transparent parts that allow first illuminating light 108, second illuminating light 110, first incident light 116, and second incident light 118 passing through housing 618. Housing 618 is rotated along an arrow 620, preferably but not limited to, around an axis passing through a center 616 of first FOV 610. Housing 618 may be rotated by a standard and/or specially designed mechanical means.

Figure 7A:
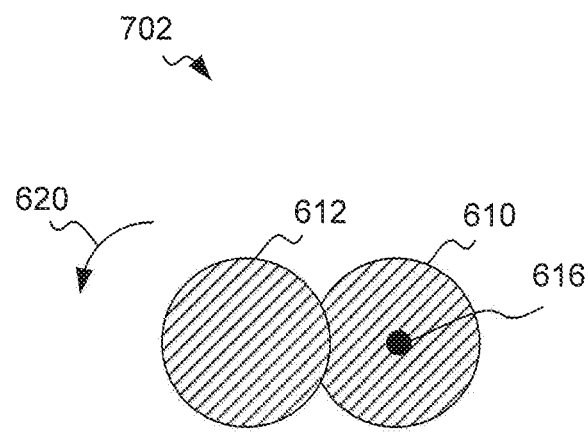
FIG. 7A shows two FOVs combined as a FOV by image stitching according to an embodiment of the present invention.

FIG. 7A shows first FOV 610 and second FOV 612 are combined as a combined FOV 702 by stitching images of first FOV 610 and second FOV 612 using standard and/or special image stitching algorithms, according to an embodiment of the present invention. Since the relative location of first FOV 610 and second FOV 612 is known, because angle β 608 between first incident light 116 and second incident light 118 is known, no overlapping image is required in image stitching. For example, FIG. 7A shows first FOV 610 and second FOV 612 having overlapping image in an embodiment.

Figure 7B:
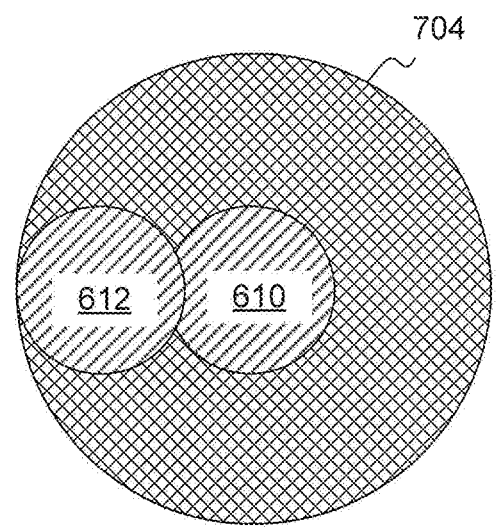
FIG. 7B shows a resultant FOV after the endoscope is rotated 360 degree according to an embodiment of the present invention.

FIG. 7B shows a resultant FOV 704 after endoscope 600 is rotated 360 degree along arrow 620 around an axis passing center 616 of first FOV 610, according to an embodiment of the present invention. All images of first FOV 610 and second FOV 612 captured within 360 degree circle are properly stitched together to form a combined image of resultant FOV 704 using standard and/or special image stitching algorithms. Resultant FOV 704 is significantly larger than first FOV 610 or second FOV 612 alone, also larger than a combination of first FOV 610 and second FOV 612, e.g., combined FOV 702.

Figure 8:
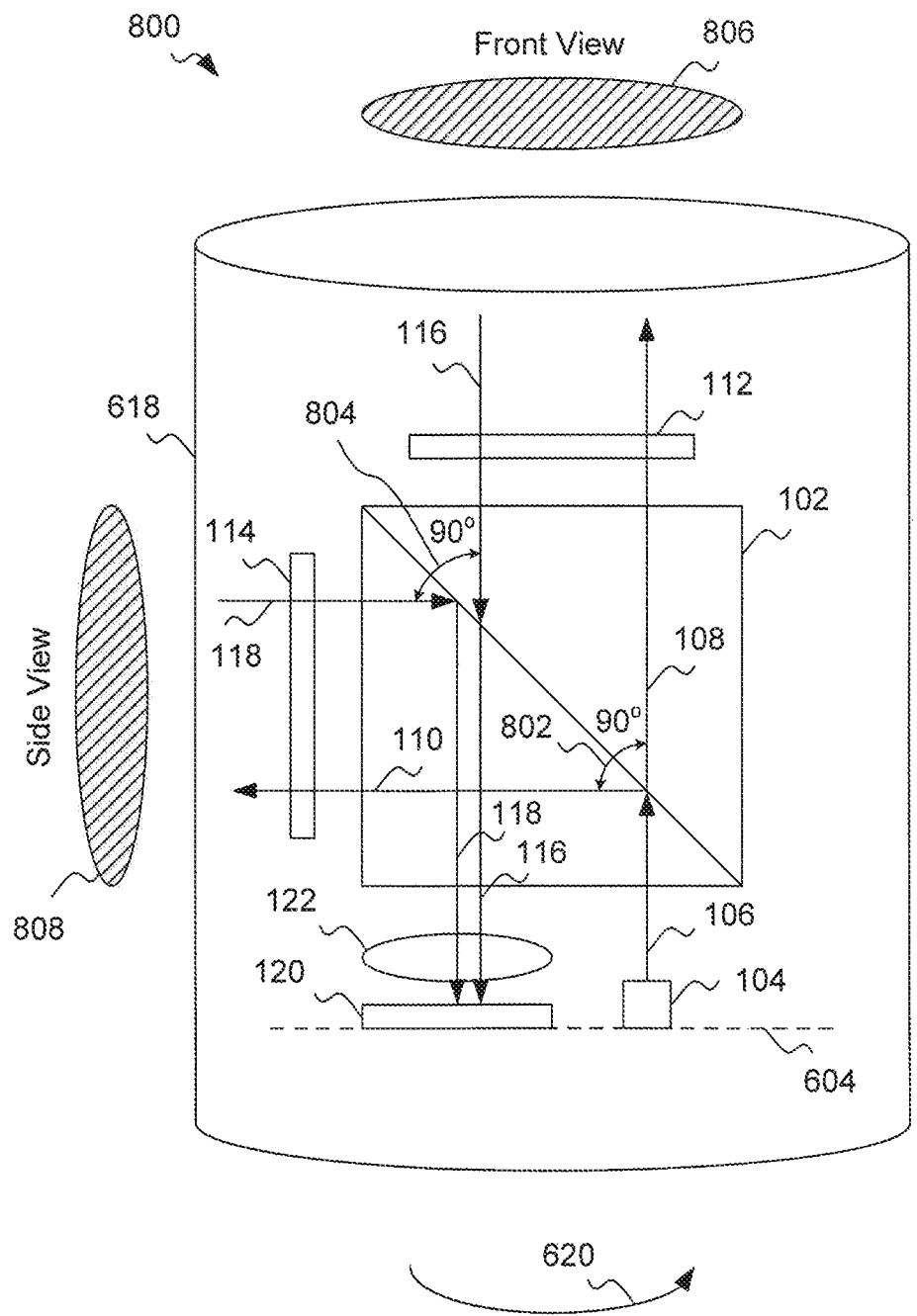
FIG. 8 schematically illustrates an exemplary rotated endoscope using a non-tilted light splitting device according to an embodiment of the present invention.

FIG. 8 illustrates an exemplary endoscope 800 according to an embodiment of the present invention. FIG. 8 is similar to FIG. 6, except the following. Light splitting device 102 together with first color filter 112 and second color filter 114 are not tilted relative to plane 604 of light source 104 and image sensor 120. An angle 802 between first illuminating light 108 and second illuminating light 110 is 90 degree. An angle 804 between first incident light 116 and second incident light 118 before combined by light splitting device 102 is also 90 degree. Accordingly, a first FOV 806 provided by first incident light 116 is a front view, and a second FOV 808 provided by second incident light 118 is a side view. Front view and side view are perpendicular. Rotating housing 618 of endoscope 800 along arrow 620 produces a 360 degree panoramic side view after proper image stitching using standard and/or special image stitching algorithms. Beam splitter cube 102 of endoscopes 300 and 400, and dichroic mirror 502 of endoscope 500 may be used as well in endoscope 800 replacing light splitting device 102.

While the present invention has been described herein with respect to the exemplary embodiments and the best mode for practicing the invention, it will be apparent to one of ordinary skill in the art that many modifications, improvements and sub-combinations of the various embodiments, adaptations and variations can be made to the invention without departing from the spirit and scope thereof.

The terms used in the following claims should not be construed to limit the invention to the specific embodiments disclosed in the specification and the claims. Rather, the scope is to be determined entirely by the following claims, which are to be construed in accordance with established doctrines of claim interpretation. The present specification and figures are accordingly to be regarded as illustrative rather than restrictive.

What is claimed is:

1. An endoscope comprising:
a light splitting device for transmitting a first illuminating light and reflecting a second illuminating light;
a first color filter transmitting a first color, wherein the first illuminating light passes through the first color filter;
a second color filter transmitting a second color, wherein the second illuminating light passes through the second color filter, wherein the first color is different from the second color;
an imaging lens and an image sensor, wherein the light splitting device combines a first incident light of the first color and a second incident light of the second color, and wherein the first incident light of the first color and the second incident light of the second color pass through the imaging lens and form images of the first color and the second color on the image sensor, respectively, wherein the first incident light transmits through the first color filter and the second incident light transmits through the second color filter;
a light source for emitting an illuminating light comprising the first illuminating light and the second illuminating light; and
a CFA (color filter array) comprising a plurality of first CFA components of the first color and a plurality of second CFA component of the second color covering the image sensor;
wherein the CFA comprises a checkerboard pattern of the first color and the second color; and
wherein the images of the first color and the second color formed on the image sensor are separated using an interpolation algorithm;
wherein the light splitting device is tilted relative to a plane of the image sensor and the light source;
wherein the first incident light provides a first FOV (field of view) and the second incident light provides a second FOV, the first FOV and the second FOV are on a plane of a front view.

2. The endoscope of claim 1 further comprising a housing;
wherein the housing encloses the light splitting device, the first color filter, the second color the imaging lens, the image sensor, and the light source;
wherein the first illuminating light, the second illuminating light, the first incident light, and the second incident light, pass through the housing; and
wherein the housing is rotated around an axis.

3. The endoscope of claim 1, wherein the light splitting device is a beam splitter cube.

4. The endoscope of claim 3 wherein the first color filter is attached on a first side of the beam splitter cube and the second color filter is attached on a second side of the beam splitter cube, and the first side and the second side are perpendicular.

5. The endoscope of claim 3 wherein the first color filter is a first band pass multilayer coating that transmits light of the. first color and the second color filter is a second band pass multilayer coating that transmits light of the second color.

* * * * *